Figure 1:
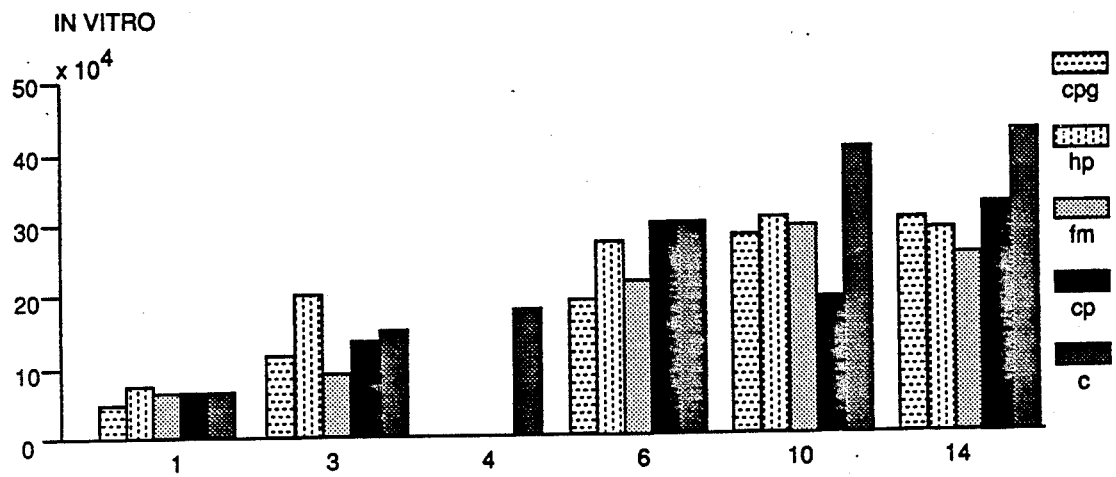

United States Patent [19]

Nieuwenhuis et al.

[11] Patent Number: 5,053,485
[45] Date of Patent: Oct. 1, 1991

[54] POLYMER LACTIDE, METHOD FOR PREPARING IT AND A COMPOSITION CONTAINING IT

[75] Inventors: Jan Nieuwenhuis, Gorinchem; Arie C. Mol, Papendrecht, both of Netherlands

[73] Assignee: C.C.A. Biochem B.V., Gorinchem, Netherlands

[21] Appl. No.: 537,152

[22] Filed: Jun. 12, 1990

Related U.S. Application Data

[63] Continuation of Ser. No. 261,785, Oct. 24, 1988, abandoned.

[30] Foreign Application Priority Data

Oct. 28, 1987 [NL] Netherlands .......................... 8702563

[51] Int. Cl.$^5$ ............................................. C08G 63/08
[52] U.S. Cl. ..................................... 528/354; 528/357
[58] Field of Search ................................ 528/354, 357

[56] References Cited

U.S. PATENT DOCUMENTS

| | | | |
|---|---|---|---|
| 3,636,956 | 1/1972 | Schneider | 528/354 X |
| 4,033,938 | 7/1957 | Augurt et al. | 528/354 |
| 4,719,246 | 1/1988 | Murdoch et al. | 528/354 X |
| 4,743,257 | 5/1988 | Törmälä et al. | 525/418 X |

FOREIGN PATENT DOCUMENTS 1595085 1/1970 Fed. Rep. of Germany .

OTHER PUBLICATIONS

Chemical Abstracts 108, 56715c (1988), (Published 2-2-2-88).
Schindler et al., "Poly(lactate) III Stereoselective Polymerization of Meso-Dilactide", Journal Poly, Sic: Part C: Polymer Letters, 26, 47-48 (1988).
Derwent abstract of German Patent No. 1,595,085.

*Primary Examiner*—Earl Nielsen
*Attorney, Agent, or Firm*—Webb, Burden, Ziesenheim & Webb

[57] ABSTRACT

A polymer lactide is prepared by the polymerization of meso-3,6-dimethyl-1,4-dioxane-2,5-dione or mesodilactide and, if desired, other monomers. The mesolactide monomer has preferably a free acid content of less than 1 meq/kg dilactide and is then polymerized in a manner known per se. The compositions containing polymesolactide obtained according to this process do not posess the typical characteristics of poly-DL-lactide, poly-D-lactide or poly-L-lactide. A shorter degradation time of a substrate based on the present polymer is unofficial for several purposes. The present polymers have a good biocompatibility and are thus suited for bone plates, clamps and sutures and controlled release of biologically active compounds. The present polylactides and/or copolymers thereof have the benefit of a good biodegradability, biocompatibility, non-toxicity and non-mutagenicity.

10 Claims, 2 Drawing Sheets

IN VITRO TEST : NUMBER OF CELLS
VERSUS DAYS

ABBREVIATIONS :

CPG = COPOLYMER GLYCOLIDE MESOLACTIDE

HP = HOMOPOLYMER MESOLACTIDE

FM = PHYSICAL MIXTURE

CP = COPOLYMER L. LACTIDE MESOLACTIDE

RESULTS OF THE SIMULATION TEST

ABBREVIATIONS AS INDICATED IN FIG. 1 AND

ME = MELINEX

PVC = POLYVINYL CHLORIDE

POLYMER LACTIDE, METHOD FOR PREPARING IT AND A COMPOSITION CONTAINING IT

This is a continuation of copending application Ser. No. 07/261,785, filed on Oct. 24, 1988, now abandoned.

The invention relates to a polymer lactide, to a method for the preparation of a polymer lactide and also to a composition which contains a polymer lactide of this type.

Polymer lactides are generally known and are used in surgery and pharmacy, for example for bone plates, clamps and sutures and controlled release of biologically active compounds. The great advantage of the use of polylactides and/or copolymers hereof is the biodegradability, biocompatibility, non-toxicity, non-mutagenicity etc.

A method of this type is known from U.S. Pat. No. 2,703,316, wherein the preparation of self-supporting thin films of polylactides is described by heating a lactide with a melting point above 120° C. to a temperature above the melting point but below 200° C. in the presence of a polyvalent metal oxide until a polymer with a tack point of 60° to 120° C. has formed. These polymers are also frequently termed polylactides because the empirical formula of these compounds is virtually the same as that of the lactide. These polylactides have an inherent viscosity of at least 0.45.

The preparation is effected by concentrating commercially available lactic acid, which contains 20 to 50% water, by distillation under atmospheric pressure at 120° to 130° C., with the removal of virtually all the water. The concentrated acid is then distilled under reduced pressure (for example 17 to 35 mm mercury pressure) to remove the water of esterification and a syrupy polylactic acid with a low molecular weight is thus obtained. A further reduction in the pressure in the distillation system to 8 to 10 mm mercury pressure and an increase in temperature to 200° to 250° C. results in the formation of the cyclic dimer lactide from the polylactic acid. This dimer distills over at 130° C. to 140° C. under a pressure of 10 to 13 mm mercury pressure. The product obtained can be purified by repeated crystallization from ethyl acetate. A polymer lactide can then be prepared from this by polymerization under the influence of a polyvalent metal salt.

Copolymers of L(-) lactides and glycolides are known from U.S. Pat. No. 3,839,297. These are prepared by heating a mixture of the monomers to 200° C. in the presence of a stannous octoate catalyst. The copolymers obtained in this way can be extruded to filaments, which are suitable as adsorbable suture.

A polymer lactide has now been found which is prepared from meso-3,6-dimethyl-1,4-dioxan-2,5-dione or mesodilactide and, if desired, other monomers. The present polymer lactide possesses a considerably shorter degradation time than the poly-DL-lactide or poly-D-lactide or poly-L-lactide. For use in surgery or pharmacy, the polymer preferably has an inherent viscosity of at least 0.5.

Together with the mesodilactide numerous other monomers can be polymerized. The other monomers can be used in an amount of at least 99% by weight, preferably at most 30% by weight. Examples of suitable other monomers are D(+)-lactide, DL-lactide, L(−)-lactide, glycolide, β-propiolactone, β-butyrolactone, γ-butyrolactone, 2-keto-1,4-dioxane, γ-valerolactone, ε-caprolactone, pivalolactone, α,α-diethylpropiolactone, 2,5-diketomorpholine, ethylene carbonate, ethylene oxalate; intermolecular cyclic diesters of α-hydroxybuteric acid, α-hydroxyvaleric acid, α-hydroxyisovaleric acid, hydroxycaproic acid and 2-hydroxyisocaproic acid.

In the purification of the crude DL-lactide use is made of conventional, inexpensive solvents, such as toluene, benzene and diethyl ether. The DL-lactide crystallized, for example, in toluene can be separated simply from the mother liquor, mainly consisting of mesolactide and toluene. After evaporating this mother liquor a liquid remains which consists of the mesolactide, free acids and byproducts. By good cooling the mesolactide can be removed from this mother liquor by crystallization and separating the crystals. This initial "crude mesolactide" can be further purified in two or more crystallization steps, a powdery, crystalline mesolactide ultimately being obtained which is characterized by a free acid content of less than 1 meq/kg and a melting point of 43° to 44° C. The low free acid content is important for the preparation of polymesolactide with a high molecular weight. When a mesolactide with a free acid content greater than 1 meq/kg is used it is found that this does not result in high molecular weights.

The recrystallization of the mesolactide can be effected from various solvents, such as ethanol, cyclohexane, toluene/cyclohexane (1:1), toluene/ethanol (1:1) and methyl ethyl ketone. Isopropyl alcohol (IPA) should, however, be preferred. It is also important to allow the recrystallization to proceed rapidly. This is in connection with the hydrolysis/decomposition of the mesolactide. If the crystallization step lasts too long, the free acid content of the final mesolactide will be too high, while the yield will be too low.

An advantageous crystallization can be carried out as follows.

30 to 140% weight mesolactide is dissolved in isopropanol at a temperature of, preferably 30° to 40° C. Once the solid has dissolved, the solution is cooled rapidly to 0° to 10° C. The mother liquor and the mesodilactide are separated with the aid of a filter or centrifuge. The entire procedure is carried out under an inert atmosphere of, preferably, dry $N_2$ (in gas form) or argon (in gas form). This can be repeated once or several times, a mesolactide with a free acid content of less than 0.1 meq/kg and a melting point of 43° C. (after drying of the crystal under severely reduced pressure) being obtained.

It was found that the conventional method for the recrystallization of isomeric lactides is not suitable in the case of the mesolactides. Conventional solvents for the purification of lactides are toluene, benzene (aromatic) and diethyl ether. However, these do not give satisfactory purification in this case.

If the mesolactide has to be kept or stored for a prolonged period this should preferably be carried out at lower temperature and in an inert gas atmosphere.

For bulk homopolymerization of the mesolactide use can be made of catalysts and reaction conditions customary for lactide polymerization (see, inter alia, U.S. Pat. No. 3,839,297). To promote the comparability of the examples, only tin octoate (stannous 2-methyl-hexanoate) dissolved in toluene has been used here; however, other catalysts can also be employed. SnO and ZnO, inter alia, may be mentioned in this context.

The polymerization temperature can vary from 60° to 180° C., but the polymerization is preferably carried out at a temperature of 80° to 120° C.

The polymerizations are preferably carried out in an inert gas (dry $N_2$) atmosphere or under strongly reduced pressure ($P<10^{-2}$ mbar, $P>10^{-7}$ mbar). The reaction times are preferably 3 to 24 hours.

It is surprising that the polymesolactides according to the invention do not, as was to some extent to be expected, possess the typical characteristics of poly-DL-lactide, poly-D-lactide or poly-L-lactide. These three last-mentioned polymers are characterized by very long degradation times (longer than 200 days) in experiments in physiological saline solutions at 37° C. Like poly-DL-lactide, polymesolactide is an amorphous polymer. The great difference from the poly-DL-lactide is the appreciably faster degradation time of the polymesolactide. The degradation times cited in the examples were determined in vitro at 37° C. over a prolonged period (a maximum of 160 days) and in a medium of phosphate buffer, salt and water (physiological saline solution).

The mesolactide cannot only be polymerized in bulk but can also be polymerized under other reaction conditions, such as from a solution. In Example VI a polymerization in toluene under a layer of nitrogen (in gas form) at elevated temperature is described.

Examples VII to IX inclusive give several possibilities for the preparation of polymers in which the mesolactide is one of the monomers. Other comonomers, such as already mentioned above, can, however, also be used.

In addition to the true "chemical" copolymers, the polymesolactide can also be processed in physical mixtures. These physical mixtures can contain a biologically active substance which is released as degradation of the polymer progresses; these physical mixtures can, however, also consist of a physical mixture with another polymer. An accelerated degradation of a substrate produced therefrom is still obtained with an amount of not more than 99% by weight other polymer. Preferably, not more than 50% by weight other polymer is used in a mixture of this type.

It can be seen from Examples XII to XIV inclusive that the addition of mesopolylactides to the other polylactides D, DL and L has a great influence on the in vitro behaviour of the physical mixtures obtained in respect of degradation time in comparison with homopolymers.

It is known that it is possible to obtain a good indication of the biocompatibility of polymers by carrying out in vitro and simulation tests. Use is made of cell cultures for these tests. In Examples XIV and XV these in vitro and simulation tests are carried out with 4 mesopolymers. It can be seen from these examples that the mesopolymers are well able to meet the requirements as biomaterials.

It is also seen that a reduced cell growth occurs in the case of the materials according to the invention which degrade most rapidly. This is ascribed to the acidification which occurs during the degradation. A strong acidification inhibits cell growth.

When choosing the material to be used, the aim will therefore have to be to obtain a good balance between the cell growth which occurs and the degradation of the material. This is needed to achieve optimum utilization of the great advantage of the material in question, which can be biologically degraded and can be replaced by new bone tissue.

Tests carried out confirm the good biocompatibility of the polymers in question. It is true that from the morphological standpoint there are some odd deviations. Frequently cells are seen which contain very large numbers of small holes or are torn; however, this is not serious. The cause is probably the absorption of the cells on the underlayer, which can differ for the diverse materials. As a result, shrinkage can occur during drying.

EXAMPLE I

Bulk homopolymerization 30 g mesolactide with a free acid content of less than 0.1 meq/kg are introduced with the aid of a small funnel under dry $N_2$ into a glass ampoule with a capacity of 50 ml. 0.23 ml of a 25.2% by weight solution of tin octoate in toluene are added, likewise under dry $N_2$. The filled ampoule is then brought under strongly reduced pressure ($P<0.1$ mbar) and rinsed three times with dry and oxygenfree $N_2$. After this rinsing cycle the ampoule is brought under strongly reduced pressure ($P<0.01$ mbar) for one and a quarter hours.

The ampoule is melted down under this pressure with the aid of a propane-oxygen burner.

The polymerization is carried out for 2 hours at 123° C. On completion of the reaction a glass-clear polymer is obtained with an intrinsic viscosity of 2.58 and a glass transition temperature (Tg) of 27° C.

After this time the monomer concentration in the polymer is less than 2% by weight, which corresponds to a conversion of more than 98%.

The polymer is purified by dissolving the whole in distilled chloroform and then pouring into the precipitant (hexane). Ethanol or a mixture of hexane and ethanol is also suitable. After cooled drying of the fibrelike material under strongly reduced pressure a good free-flowing powder is obtained.

EXAMPLE II

Bulk homopolymerization 26 g mesolactide with a free acid content of less than 0.1 meq/kg is processed in the manner described in Example I except that 0.065 ml 25.2% by weight solution of tin octoate is added and a reaction time of 18.25 hours is employed. The polymer obtained has an intrinsic viscosity of 3.62.

EXAMPLE III

Bulk homopolymerization 27 g mesolactide with a free acid content of less than 0.1 meq/kg are used in the manner described in Example I, except that 0.31 ml 5% by weight solution of tin octoate are employed (M/I 5000). A reaction time of 112 hours is employed. The polymer obtained has an intrinsic viscosity of 3.82.

COMPARISON EXAMPLE I

Bulk homopolymerization (with a free acid content greater than 1 meq/kg).

The procedure described in Example I is followed and 23.3 g mesolactide with a free acid content of 1.2 meq/kg are employed. The following changes are made to the recipe: 0.18 ml 25.2% tin octoate (M/I 1,500). A reaction temperature of 120° C. and a reaction time of 3 hours 5 minutes.

A polymer with an intrinsic viscosity of 0.294 is obtained in this way.

It can be clearly seen from this that a less good polymer is obtained if a free acid content greater than 1 meq/kg is employed.

EXAMPLE IV

Bulk homopolymerization.

The procedure described in Example I is followed and 27 g mesolactide with a free acid content of less than 0.1 meq/kg is used.

The following changes are made to the recipe described in Example I: reaction time 10 minutes (at a reaction temperature of 123° C.); 0.30 ml 5% by weight stannous octoate is added. The polymer obtained has an intrinsic viscosity of 0.40. The conversion is greater than 95%.

EXAMPLE V

Solution polymerization 100 g mesolactide with a free acid content of less than 0.1 meq/kg are added to 300 ml toluene in a roundbottomed flask provided with a nitrogen inlet, a stirrer, a heating jacket and a condenser. Nitrogen is passed through the solution for 2 hours and during this time the temperature of the solution is gradually raised to 80° C. 1 ml of a 5% by weight solution of tin octoate and toluene is then added. After 7 hours' reaction the reaction is stopped. After pouring out the dissolved polymesolactide into hexane, separating off and drying, the viscosity is determined. A polymesolactide with an intrinsic viscosity of 0.58 is obtained.

EXAMPLE VI

Bulk polymerization:copolymer

The procedure described in Example I is followed and 7.74 g mesolactide and 28.65 g L-lactide are used, both with a free acid content of less than 0.1 meq/kg. After a reaction time of 50 minutes at a temperature of 120° C. and using a M/I=1500 (ratio of monomer:initiator on molar basis), the polymer obtained has, after working up, an intrinsic viscosity of 4.22. The yield is 99%.

EXAMPLE VII

Bulk polymerization:copolymer

The procedure described in Example VI is followed and 11.21 g mesolactide and 25.04 g L-lactide are used, both with a free acid content of less than 0.1 meq/kg. After a reaction time of 3.05 hours at 120° C. and using a M/I=2130, the polymer obtained has an intrinsic viscosity of 3.7.

EXAMPLE VIII

Bulk polymerization:copolymer

The procedure described in Example VI is followed and 15.31 g mesolactide and 15.12 g glycolide are used, both with a free acid content of less than 0.1 meq/kg. After a reaction time of 17 hours at 120° C. and using a M/I=1500, a polymer is obtained which has an intrinsic viscosity of 1.16 when measured in hexafluoroisopropanol.

EXAMPLE IX

Degradation tests on polymesolactide homopolymer

A film is cast from a 25% by weight solution of polymesolactide in chloroform and dried. The film is cut into pieces 15 by 6 cm. The pieces are kept for a prolonged period at 37° C. in an aqueous physiological saline solution with a pH of 7.4 (provided with phosphate buffer). The thickness of the film was 25 m. At fixed times a portion of the film was removed from the bath, rinsed carefully and dried. The intrinsic viscosity, the number of days, the molar mass (calculated using the Mark Houwink constants for poly-DL-lactide), means viscosity molecular weight and the percentage of the initial mass of the film are shown in Table A.

TABLE A

| days | intrinsic viscosity | Mv (D.L.) | % mass |
|---|---|---|---|
| 0 | 0.79 | 41,100 | 100 |
| 15 | 0.42 | 18,100 | 100.2 |
| 49 | 0.18 | 6,000 | 81.7 |
| 84 | 0.04 | 800 | 18.1 |
| 116 | 0.00 | 0 | 0.5 |
| 169 | 0.00 | 0 | 0.4 |

EXAMPLE X

Degradation tests on polymesolactide homopolymer

The procedure described in Example IX is followed but a 5% by weight solution in chloroform is used and a film with a thickness of 20 μm is produced. The measurements shown in Table B are obtained.

TABLE B

| days | intrinsic viscosity | Mv (D.L.) | % mass |
|---|---|---|---|
| 0 | 1.07 | 63,000 | 100 |
| 28 | 0.73 | 37,000 | 100.4 |
| 42 | 0.59 | 28,000 | 98.6 |
| 84 | 0.46 | 20,000 | 98.8 |
| 102 | 0.28 | 10,700 | 99.5 |
| 155 | 0.1 | 2,800 | 29.9 |

EXAMPLE XI

Degradation behaviour of physical mixtures of poly-L-lactide/polymesolactide

A film is cast in the manner described in Example IX from a 5% by weight solution of poly-L-lactide/polymesolactide in chloroform. The poly-L-lactide/polymeso ratios shown in Table C are used.

The degradation tests are carried out in the manner described in Example IX.

The mass percentages of mesolactide in the physical mixture, the intrinsic viscosity and mass loss in % are given in Table C.

TABLE C

| % poly-meso | Viscosity and mass in % as a function of the number of days | | | | | | | | | | | |
|---|---|---|---|---|---|---|---|---|---|---|---|---|
| | 0 | | 15 d | | 49 d | | 84 d | | 116 d | | 169 d | |
| | visc. | % m | visc. | % m | visc. | % m | visc. | % m | visc. | % m | visc. | % m |
| 0 | 5,88 | 100 | 5,49 | 100 | 4,69 | 100,3 | 4,29 | 100,3 | 3,78 | 105,8 | 3,23 | 100,5 |
| 25 | 5,07 | 100 | 3,98 | 98,6 | 2,53 | 99,1 | 1,99 | 90,3 | 1,26 | 82,2 | 1,05 | 74 |
| 50 | 3,78 | 100 | 2,84 | 99 | 2,04 | 99,1 | 1,75 | 92,7 | 1,68 | 68 | 1,7 | 51,7 |

TABLE C-continued

| % poly-meso | Viscosity and mass in % as a function of the number of days | | | | | | | | | | | |
|---|---|---|---|---|---|---|---|---|---|---|---|---|
| | 0 | | 15 d | | 49 d | | 84 d | | 116 d | | 169 d | |
| | visc. | % m | visc. | % m | visc. | % m | visc. | % m | visc. | % m | visc. | % m |
| 75 | 2,43 | 100 | 1,71 | 99,8 | 1,13 | 98,6 | 0,72 | 99,6 | 0,42 | 79,4 | 0,67 | 37,1 |
| 100 | 0,79 | 100 | 0,42 | 100,2 | 0,18 | 81,7 | 0,04 | 18,1 | — | 0,5 | — | 0,4 |

EXAMPLE XII

Degradation behaviour of physical mixtures of poly-DL-lactide/polymesolactide

The procedure described in Example XI is followed. However, poly-DL-lactide is used as the second component in the physical mixture. The results are shown in Table D.

TABLE D

Viscosity and mass in % as a function of the number of days
Poly-DL-lactide/poly-meso-lactide: physical mixtures

| % poly-meso | 0 | | 15 d | | 49 d | | 84 d | | 116 d | | 169 d | |
|---|---|---|---|---|---|---|---|---|---|---|---|---|
| | visc. | % m | visc. | % m | visc. | % m | visc. | % m | visc. | % m | visc. | % m |
| 0 | 2,24 | 100 | 1,42 | 101,2 | 0,95 | 98,9 | 0,7 | 99,1 | 0,47 | 102,3 | 0,28 | 97,4 |
| 25 | 2 | 100 | 1,17 | 100,9 | 0,78 | 99,7 | 0,54 | 99,7 | 0,36 | 102,4 | 0,14 | 84 |
| 50 | 1,5 | 100 | 0,87 | 100,9 | 0,6 | 99,7 | 0,42 | 99,7 | 0,2 | 100,2 | 0,06 | 31,2 |
| 75 | 1,94 | 100 | 1,15 | 98,8 | 0,74 | 98,8 | 0,42 | 99,9 | 0,09 | 78,1 | — | 2,9 |
| 100 | 0,79 | 100 | 0,42 | 100,2 | 0,18 | 81,7 | 0,04 | 18,1 | — | 5 | — | 0,4 |

EXAMPLE XIII

Degradation behaviour of physical mixtures of poly-D-lactide/polymesolactide

The procedure described in Example XI is followed. However, poly-D-lactide is used as the second component in the physical mixture. The results are shown in Table E.

TABLE E

Viscosity and mass in % as a function of the number of days
Poly-D-lactide/poly-meso-lactide physical mixtures

| % poly-meso | 0 | | 15 d | | 49 d | | 84 d | | 116 d | | 169 d | |
|---|---|---|---|---|---|---|---|---|---|---|---|---|
| | visc. | % m | visc. | % m | visc. | % m | visc. | % m | visc. | % m | visc. | % m |
| 0 | 8,31 | 100 | 5,91 | 99,1 | 2,51 | 98,3 | 1,86 | 99 | 1,29 | 99,8 | 1,08 | 97,9 |
| 25 | 5,58 | 100 | 3,86 | 97,4 | 2,59 | 97,9 | 1,9 | 91,8 | 1,4 | 74,7 | 1,66 | 83,4 |
| 50 | 3,98 | 100 | 3,06 | 96,8 | 2,37 | 97,5 | 1,91 | 99,2 | 0,56 | 80,3 | 1,82 | 60,8 |
| 75 | 2,54 | 100 | 1,77 | 97,3 | 1,16 | 98,3 | 0,74 | 97,8 | 0,38 | 62,3 | 0,47 | 28,8 |
| 100 | 0,79 | 100 | 0,42 | 100,1 | 0,18 | 81,7 | 0,04 | 18,1 | — | 0,5 | — | 0,4 |

EXAMPLE XIV

In vitro test

Films are cast from a mesolactide homopolymer ($\eta$ intr=3.6), a L-lactide/mesolactide copolymer (50/50, $\eta$ intr=2.4), a physical mixture of polymesolactide/poly-L-lactide (50/50, $\eta$ intr, meso=1.0 intr, L=7.8) and a mesolactide/glycolide copolymer (90/10, $\eta$ intr=2.6) and dried. After drying the films are rinsed for 12 hours in tap water to remove any residual solvent (chloroform). The films are then dried and punched to give circles 3 cm in diameter. The base of TCPS (tissue culture polystyrene) culture dishes is then covered with these films, after which cell cultures of serially cultured rat middle ear epithelium are carried out at 37° C. on these. Growth curves of the cultures were determined by determining the cell count after trypsination on days 1, 3, 6, 10 and 14. TCPS was included in the experiment as control.

FIG. 1 shows the number of cells as a function of the number of days.

EXAMPLE XV

Extracts were made from the films mentioned in example XIV by exposing identical portions of the films to a pseudo-extracellular fluid for 62 hours at 115° C. The resulting salt solution later, after filtration, constitutes the basis for a culture medium in which cells are cultured. This medium is added on day 3 after the start of the culture in order to guarantee a good initial culture; the culture is carried out at 37° C. The cell counts are determined after 4, 6, 10 and 14 days.

Melinex (positive control) and PVC (polyvinyl chloride: negative control) are included as control.

Figure 2:
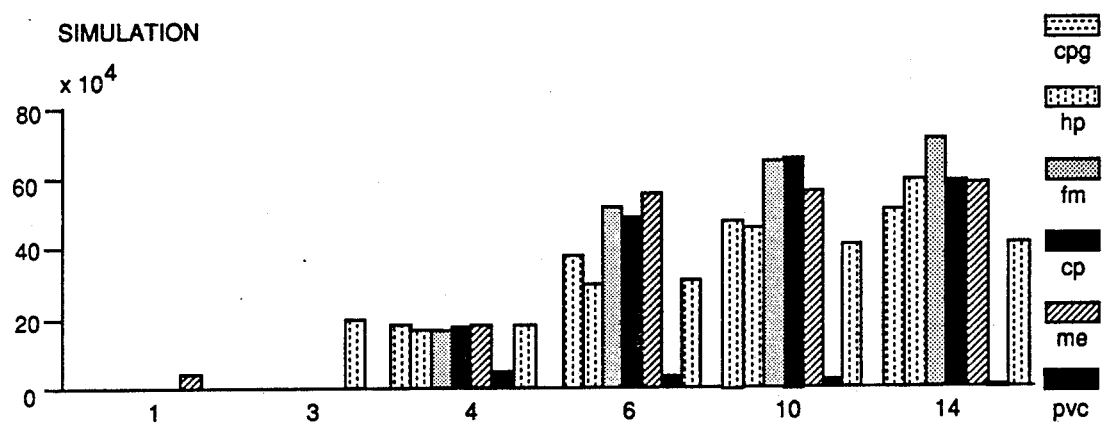

In FIG. 2 the cell counts are plotted against the time (in days).

DETERMINATION OF FREE ACID

Principle

The free acid in the sample is titrated to an end point with phenol red in a non-aqueous system using methoxide in methanol.

Reagents and apparatus

1. Absolute methanol, reagent quality, must be kept dry.
2. Potassium methoxide—approximately 0.01N solution in absolute methanol. (Obtained from Alpha Inorganic, Ventron, Beverly, Mass.). Approximately 0.34 g KOCH$_3$ is dissolved in absolute methanol in a volumetric flask with a capacity of 250 ml.
3. Benzoic acid, reagent quality.
4. Phenol red indicator, 0.05% weight/vol in absolute methanol (a small quantity freshly prepared each day).
5. Balance with a sensitivity of 0.01 mg.
6. Burettes with a capacity of 10 ml.

7. Magnetic stirrer and a stirrer coated with Teflon.
8. Dry nitrogen, regulator and tubes.
9. Vacuum flasks with a capacity of 50 ml.
10. Weighing dishes with a capacity of 1 ml or equivalent.

Standardization

1. Accurately weigh out approximately 5 mg benzoic acid as the first standard in each of two small weighing dishes (item 10).
2. Introduce 15 ml absolute methanol in the vacuum flask, which contains a rod stirrer, while a gentle stream of dry nitrogen flows through the side arm. 3. Add 5 to 6 drops phenol red indicator.
4. Titrate (2) above with absolute methanol/$KOCH_3$ solution to the end point with phenol red.
5. Add one dish with primary benzoic acid standard to the solution in step 4.
6. Titrate to the same shade of red as in step 4, with stirring.
7. Titrate the second primary standard in the same way.
8. Calculate the normality of the potassium methoxide. $N = mg$ benzoic acid ml $KOCH_3$ solution $\times 122.1$.
9. Mean the value obtained in steps 6 and 7.

Method

1. Proceed as in standardization steps 2, 3 and 4.
2. Accurately weigh approximately 0.4–0.5 g sample and introduce it into the vacuum flask. Expose the sample to the atmosphere as little as possible (the sample is difficult to dissolve in absolute methanol and dissolves slowly. It must be as free from lumps as possible).
3. Back-titrate to the same shade of red as in step 1 of the standardization, with stirring (the end point must be stable as long as a gentle stream of nitrogen is maintained).

CALCULATION

| milli-equivalent acid | ml base $\times$ N |
| grams sample | grams sample |

These values must be converted to meq/kg by multiplying by a factor of 1,000.

In this context it is also pointed out that it is very important to handle and store the monomer properly (i.e. avoid exposure to moisture from the air, reduce the air to 0.1 mm from half an hour before storage, keep at a temperature lower than 4° C. in a plastic bottle in a plastic bag which contains dessicant).

We claim:

1. A polymer composition, comprising: a surgical and pharmaceutical grade polymer lactide having at least two co-monomers therein, wherein at least one of said co-monomers is meso-3,6-dimethyl-1,4-dioxan-2,5-dione.

2. The polymer composition according to claim 1 wherein said co-monomers other than meso-3,6-dimethyl-1,4-dioxan-2,5-dione comprise at most 99% of the polymer composition.

3. The polymer composition according to claim 2 wherein said co-monomers other than meso-3,6-dimethyl-1,4-dioxan-2,5-dione comprise at most 30% of the polymer composition.

4. The polymer composition according to claim 3 wherein said co-monomers other than meso-3,6-dimethyl-1,4-dioxan-2,5-dione are selected from the group consisting of L-lactide, glycolide, DL-lactide, γ- and δ-valerolactone, D-lactide and δ-caprolactam are used as other monomers.

5. The polymer composition according to claim 1 wherein said meso-3,6-dimethyl-1,4-dioxan-2,5-dione has a free acid content of less than 1 meq/kg.

6. Method for the preparation of a surgical and pharmaceutical grade polymer lactide, characterized in that meso-3,6-dimethyl-1,4-dioxan-2,5-dione is combined with at least one other co-monomer in the polymer composition.

7. Method according to claim 6 wherein a co-monomer selected from the group consisting of L-lactide, glycolide, DL-lactide, γ- and δ-valerolactone, D-lactide and ε-caprolactam is included within the polymer composition.

8. The method according to claim 6 wherein a biologically active substance is incorporated therein.

9. The polymer composition according to claims 5 wherein the co-monomers other than meso-3,6-dimethyl-1,4-dioxane-2,5-dione comprise not more than 99% by weight of the composition.

10. The polymer composition according to claim 9 wherein said co-monomers other than meso-3,6-dimethyl-1,4-dioxane-2,5-dione comprise not more than 50% by weight of the composition.

* * * * *

UNITED STATES PATENT AND TRADEMARK OFFICE
CERTIFICATE OF CORRECTION

PATENT NO. : 5,053,485

DATED : October 1, 1991

INVENTOR(S) : Jan Nieuwenhuis and Arie C. Mol

It is certified that error appears in the above-identified patent and that said Letters Patent is hereby corrected as shown below:

On the title page, item [56], References Cited Other Publications "Journal Poly, Sic:" should read --Journal Poly, Sci:--.

Column 2 Line 39 after "140%" insert --by--.

Column 9 Line 13 begin new paragraph with "3."

Signed and Sealed this

Fifteenth Day of November, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,053,485
DATED : October 1, 1991
INVENTOR(S) : Jan Nieuwenhuis and Arie C. Mol It is certified that error appears in the above-indentified patent and that said Letters Patent is hereby corrected as shown below:

Column 10, line 40 (claim 9), "according to claims 5" should read --according to any one of claims 1-5--.

Signed and Sealed this

Fourteenth Day of February, 1995

Attest:

BRUCE LEHMAN

*Attesting Officer*    *Commissioner of Patents and Trademarks*